United States Patent [19]
Rubio et al.

[11] Patent Number: 5,576,187
[45] Date of Patent: Nov. 19, 1996

[54] STANDARDS FOR PHOSPHOROTHIOATE INSECTICIDE IMMUNOASSAYS

[75] Inventors: Fernando M. Rubio, Doylestown, Pa.; Timothy S. Lawruk, New Castle, Del.

[73] Assignees: Ohmicron Technology, Inc., Wilmington, Del.; DowElanco, Indianapolis, India.

[21] Appl. No.: 303,343

[22] Filed: Sep. 9, 1994

Related U.S. Application Data

[63] Continuation-in-part of Ser. No. 127,583, Sep. 28, 1993, abandoned.

[51] Int. Cl.$^6$ .................................................. G01N 33/353
[52] U.S. Cl. ..................... 435/7.93; 435/967; 436/526; 436/815
[58] Field of Search ................................... 435/7.93, 967, 435/975; 436/526, 815

[56] References Cited

FOREIGN PATENT DOCUMENTS

WO9100294  1/1991  WIPO.

OTHER PUBLICATIONS

D. McAdam et al., Issued 1992, Journal of Agricultural and Food Chemistry, "Mono- and Polyclonal Antibodies to the Organophosphate Fenitrothion. 1. Approaches to Hapten-–Protein Conjugation," vol. 40, pp. 1466–1470.

J. Skerritt et al., Issued 1992, Journal of AOAC International, "Enzyme–Linked Immunosorbent Assay for Quantitation of Organophosphate Pesticides: Fenitrothion, Chlorpyrifos–methyl, and Pirimiphos–methyl in Wheat Grain and Flour–Milling Fractions," vol. 75, pp. 519–528.

J. Skerritt et al., Published 1991, American Chemical Society, ACS Symposium Series, "Testing Cereal Products and Samples by Immunoassay," Chapter 11, pp. 124–138.

Südi et al., Issued 1988, Kieler Milchwirtschaftliche Forschungsberichte, "Studies on the development of an immuno assay for the group–specific detection of the diethyl ester of phosphates, thiophosphates, dithiophosphates and phosphonates," vol. 40, pp. 179–203.

A. Hill et al., Issued 1992, Journal of Agricultural and Food Chemistry, "Mono– and Polyclonal Antibodies to the Organophosphate Fenitrothion. 2. Antibody Specificity and Assay Performance," vol. 40, pp. 1471–1474.

H. Dahn et al., Magnetic Resonance in Chemistry, "NMR of Terminal Oxygen 9*—$^{17}$O NMR of the P—O 'Double Bond': Phosphine Oxides, Phosphinates, Phosphonates, Acylphosphonates and Related Compounds,", vol. 30, pp. 1089–1096.

*Primary Examiner*—Mary E. Ceperley
*Attorney, Agent, or Firm*—Allan H. Fried

[57] ABSTRACT

Improvements in immunoassays for chlorpyrifos and compounds structurally related to chlorpyrifos are achieved by using standards of increased stability.

39 Claims, 5 Drawing Sheets

Diethylchlorothiophosphate Stability

Fig. 5

Chlorpyrifos Standard Stability

5,576,187

STANDARDS FOR PHOSPHOROTHIOATE INSECTICIDE IMMUNOASSAYS

This application is a continuation-in-part application of application Ser. No. 8/127,583 filed Sep. 28, 1993, abandoned.

FIELD OF THE INVENTION

The invention relates to improvements in immunoassays for phosphorothioate insecticides, such as chlorpyrifos.

BACKGROUND

Chlorpyrifos and structurally related compounds have insecticidal activity against a variety of arthropods. Because of their extensive use in agriculture, it is important to be able to monitor their levels in water and food that could be ingested by humans. To that end, immunoassays utilizing antibodies against such phosphorothioate compounds as chlorpyrifos, chlorpyrifos-methyl, fenitrothion, and pirimiphos-methyl have been developed (J.H. Skerrit et al, Journal of AOAC International, Vol 75, 519 (1992); J. H. Skerrit et al; abstracts of The 106th AOAC Annual International Meeting & Exposition, Cincinnati, Ohio, 1992. p.162; PCT application PCT/AU90/00278 of J. Skerrit et al).

Normally, in an immunoassay, known quantities of the substance being assayed for; i.e., the analyte, are used as standards to calibrate the assay. Not all phosphorothioate insecticides are stable in aqueous conditions, however. Therefore, it is desirable to have a substance that will both react with antibodies such as anti-chlorpyrifos antibodies and be stable.

BRIEF SUMMARY OF THE INVENTION

The invention relates to immunoassays involving antibodies that react with chlorpyrifos or compounds structurally related to chlorpyrifos, the inventive improvement being the use of stable compounds as antibody-reactive standards in such assays. Examples of such stable compounds are diethylchlorothiophosphate, diethyl 4-methylbenzylphosphonate, and N-methyl-3,5,6-trichloro-2-pyridinone, or similar compounds. Related inventions are kits comprising the stable standards.

DESCRIPTION

In one general aspect, the invention is an immunoassay process comprising the steps of:

1) reacting a sample (preferably a solution, and more preferably an aqueous solution) with an antibody, said sample comprising an amount of analyte, said antibody reactive against said analyte, 2) reacting a known amount of a standardizing compound (preferably in solution, and more preferably in an aqueous solution) with an antibody of the same specificity as that used in step (1), 3) quantitating the amount of antibody that reacted with the sample in step (1);

4) quantitating the amount of antibody that reacted with the standardizing compound in step (2);

5) utilizing the amounts quantitated in steps (3) and (4) and the known amount in step (2) to calculate the amount of analyte present in the sample used in step (1), wherein the analyte is

[structure diagram with $R_3$, $R_4$, $X_2$, $R_2$, $X_1$, and $-O-P(=S)(OR_1)(OR_1)$ group]

wherein the standardizing compound is either

[structure: $R_7-P(=O)(OR_6)(OR_6)$ with $R_8$]

or

[structure: benzene ring with $R_{10}$, $R_{15}$, $R_{16}$, $-R_{11}-P(=O)(OR_9)(OR_9)$ with $R_{12}$]

or

[structure: pyridinone ring with $R_{14}$ substituents, $=O$, and $N-R_{13}$]

wherein $X_1$ x is C or N, $X_2$ is C if $X_1$ is C, $X_2$ is C or N if $X_1$ is N, R is $C_1-C_4$ alkyl, $R_2$ is H, $C_1-C_4$ alkyl, $NO_2$, a dialkylamino that is di($C_1-C_4$ alkyl)amino, Cl, Br, I, ($C_1-C_4$ alkyl)—S—, $C_1-C_4$ alkyl-(O=S)—, —$SO_2NH_2$, or —S—$R_5$, provided that $R_2$ is —S—$R_5$ only if $X_1$ and $X_2$ are both C and $R_2$ is in the para position (4-position on the benzene ring), $R_3$ is H, Cl, Br, or I, $R_4$ is H, Cl, Br, or I, $R_5$ is

[structure: phenyl-$O-P(=S)(OR_1)(OR_1)$]

wherein $R_6$ is $C_1-C_4$ alkyl, $R_7$ is Cl, Br, I, OH, $(CH_2)_mCH_3$, benzyl or benzyl substituted with I, Cl, Br, $CH_3$, $OCH_3$, $O(CH2)_mCH_3$, and m is an integer in the range 1 through 10 (i.e., 1, 2, 3, 4, 5, 6, 7, 8, 9, or 10)

$R_8$ is O, NH, or S, $R_9$ is H, or $C_1$–$C_4$ alkyl, $R_{10}$ is Cl, Br, I, $CH_3$, $(CH_2)_qCH_3$, $OCH_3$, or $O(CH_2)_qCH_3$, and q is an integer in the range 1 through 10, $R_{11}$ is $(CH_2)_y$, and y is an integer in the range 1 through 10

$R_{12}$ is O, NH, or S, $R_{13}$ is $CH_3$, $(CH_2)_zCH_3$, $OCH_3$, or $O(CH_2)_zCH_3$ and wherein z is an integer in the range 1 through 10, $R_{14}$ is Cl, I or Br, $R_{15}$ is H, Cl, Br, or I, $R_{16}$ is H, Cl, Br, or I, provided that $R_2$, $R_3$, and $R_4$, are not joined to $X_1$ if it is N or to $X_2$ if it is N. Otherwise, the foregoing text and diagrams in this Description section of the application are not intended to limit the positions of the three substituents, $R_2$, $R_3$, and $R_4$, to any particular position or positions on the 6-atom aromatic ring to which they are linked, except that not more than one of those three substituents can be at any given atom on the ring on a single compound, and of course none of those substituents can be at the same position occupied by the —O—PS(OR$_1$)$_2$ group. Similarly, the foregoing text and diagrams in this Description section of the application are not intended to limit the positions of the three substituents, $R_{10}$, $R_{15}$, and $R_6$, to any particular position or positions on the 6-atom aromatic ring to which they are linked, except that not more than one of those three substituents can be at any given atom on the ring on a single compound, and of course none of those substituents can be at the same position occupied by the —O—R$_{11}$PR$_{12}$S(OR$_9$)$_2$ group.

In another embodiment, the invention is a process of calibrating a standardizing compound relative to a test compound of interest in an immunoassay of interest, said process comprising the steps of:

1) reacting a known amount of test compound with an antibody,

2) reacting under the immunoassay conditions of step (1) a known amount of a standardizing compound with an antibody of the same specificity as that used in step (1) (i.e., same immunoassay conditions as step (1) except that the test compound has been replaced with the standardizing compound), 3) quantitating the amount of antibody that reacted with the test compound in step (1);

4) quantitating the amount of antibody that reacted with the standardizing compound in step (2);

5) utilizing the amounts quantitated in steps (3) and (4) and the known amounts of steps (1) and (2) to calculate the relative reactivity of the standardizing compound and the test compound under the immunoassay conditions of step (1), wherein the test compound is wherein the standardizing compound is either or or wherein $X_1$ is C or N, $X_2$ is C if $X_1$ is C, $X_2$ is C or N if $X_1$ is N,

$R_1$ is $C_1$–$C_4$ alkyl, $R_2$ is H, $C_1$–$C_4$ alkyl, $NO_2$, a dialkylamino that is di($C_1$–$C_4$ alkyl)amino, Cl, Br, I, ($C_1$–$C_4$ alkyl)—S—, $C_1$–$C_4$ alkyl-(O=S)—, —SO$_2$NH$_2$, or —S—R$_5$, provided that $R_2$ is —S—R$_5$ only if $X_1$ and $X_2$ are both C and $R_2$ is in the para position (4-position on the benzene ring)

$R_3$ is H, Cl, Br, or I, $R_4$ is H, Cl, Br, or I, $R_5$ is wherein $R_6$ is $C_1$–$C_4$ alkyl, $R_7$ is Cl, Br, I, OH, $(CH_2)_mCH_3$, benzyl or benzyl substituted with I, Cl, Br, $CH_3$, $OCH_3$, $O(CH2)_mCH_3$, and m is an integer in the range 1 through 10 (i.e., 1, 2, 3, 4, 5, 6, 7, 8, 9, or 10)

$R_8$ is 0, NH, or S, $R_9$ is H or $C_1$–$C_4$ alkyl, $R_{10}$ is Cl, Br, I, $CH_3$, $(CH_2)_qCH_3$, $OCH_3$, or $O(CH_2)_qCH_3$, and q is an integer in the range 1 through 10, $R_{11}$ is $(CH_2)_y$, and y is an integer in the range 1 through 10

$R_{12}$ is O, NH, or S, $R_{13}$ is $CH_3$, $(CH_2)_zCH_3$, $OCH_3$, or $O(CH_2)_zCH_3$ and wherein z is an integer in the range 1 through 10, $R_{14}$ is Cl, I or Br, $R_{15}$ is H, Cl, Br, or I, $R_{16}$ is H, Cl, Br, or I, provided that $R_2$, $R_3$, and $R_4$, are not joined to $X_1$ if it is N or to $X_2$ if it is N.

It is preferred that if $R_2$ is dialkylamino then it be used when $X_1$ and $X_2$ are both N and that it be at that carbon on the aromatic ring immediately adjacent to both N atoms.

It is preferred that when $R_2$ is $NO_2$, $C_1$-$C_4$ alkyl-S—, $C_1$-$C_4$ alkyl-(O=S)—, —$SO_2NH_2$, that $X_1$ and $X_2$ both be C and that $R_2$ be at the 4-position on the aromatic ring; in those cases it is even more preferred that $R_3$ and $R_4$ both be H.

Particularly preferred standardizing compounds are N-methyl-3,5,6-trichloro-2-pyridinone, diethyl 4-methylbenzylphosphonate, and diethylchlorothiophosphate.

N-methyl-3,5,6-trichloro-2-pyridinone, is a compound described above with $R_{13}$ and $R_{14}$ and wherein $R_{13}$ is methyl and $R_{14}$ is Cl. It was obtained from DowElanco, Indianapolis, Ind.

Diethyl 4-methylbenzylphosphonate, is a compound described above with $R_9$, $R_{10}$, $R_{11}$, and $R_{12}$, and wherein $R_9$ is ethyl, $R_{10}$ is methyl, $R_{11}$ is $CH_2$, $R_{12}$ is O and $R_{15}$ and $R_{16}$ are H. It is commercially available from Lancaster Synthesis, Windham, N.H.

Diethylchlorothiophosphate is the compound above with $R_6$, $R_7$, and $R_8$, and wherein $R_6$ is ethyl, $R_7$ is Cl and $R_8$ is S. It is commercially available from Aldrich Chemical Company, Milwaukee, Wis.

"$C_1$-$C_4$ alkyl" includes methyl, ethyl, n-propyl, isopropyl, n-butyl, sec-butyl, isobutyl, and tert-butyl. An example of "($C_1$-$C_4$)alkyl S—" is "—$SCH_2CH_3$".

In $C_1$-$C_4$ alkyl-(O=S)—, the $C_1$-$C_4$ alkyl group is directly linked to the sulfur atom and the sulfur atom is also directly linked to both the oxygen atom and the aromatic ring of the analyte or test compound.

It is preferred that if $R_3$ is Cl, Br, or I, then both $R_2$ and $R_4$ are either H, Cl, Br, or I. It is more preferred that if $R_3$ is Cl, Br, or I, then $R_2$, $R_3$, and $R_4$ be the same.

It is preferred that if $R_{15}$ is Cl, Br, or I, then both $R_{10}$ and $R_{16}$ are either H, Cl, Br, or I. It is more preferred that if $R_{15}$ is Cl, Br, or I, then $R_{10}$, $R_{15}$, and $R_{16}$ be the same.

Preferred analyte and test compounds are: chlorpyrifos, chlorpyrifos-methyl, diazinon, fenitrothion, parathion-methyl, parathion, fensulfothion, fenthion, pyrimiphos-ethyl, pyrimiphos-methyl, dicapthon, cythioate, and temephos.

Chlorpyrifos is O,O-diethyl O-(3,5,6-trichloro-2-pyridyl)phosphorothioate (CAS: 2921-88-2).

Chlorpyrifos-methyl is O,O-dimethyl O-(3,5,6-trichloro-2-pyridyl)phosphorothioate. (CAS: 598-13-0).

Diazinon is O,O-odiethyl O-isopropyl-6-methylpyfimidin-4-yl phosphorothioate (CAS:333-41-5).

Fenitrothion is O,O-dimethyl O-(3-methyl-4-nitrophenyl)phosphorothioate (CAS: 122-14-5).

Parathion-methyl is O,O-dimethyl O-4-nitrophenyl phosphorothioate (CAS:298-00-0).

Parathion is O,O-diethyl O-4-nitrophenyl phosphorothioate (CAS: 56-38-2).

Fensulfothion is O,O-diethyl O-[p-(methylsulfinyl)phenyl] phosphorothioate (CAS: 115-90-2).

Fenthion is O,O-dimethyl O-[3-methyl-4(methylthio)phenyl]phosphorothioate (CAS:55-38-9).

Pyfimiphos-ethyl is O-2-diethylamino-6-methylpyrimidin-4-yl O,O-diethylphosphorothioate (CAS:23505-41-1).

Pyfimiphos-methyl is O-2-diethylamino-6-methylpyfimidin-4-yl O,O-dimethylphosphorothioate (CAS: 29232-93-7).

Dicapthon is O(2-chloro-4-nitrophenyl) O,O-dimethyl phosphorothioate (CAS: 2463-84-5).

Cythioate is O,O-dimethyl O-p-sulfamoylphenyl phosphorothioate (CAS:115-93-5).

Temephos O,O,O',O'-tetramethyl O,O'-thiodi-p-phenylene bis(phosphorothioate) (CAS:3383-96-8).

If the analyte of interest is chlorpyrifos, a preferred way to do the assay is to first do the assay with a known amount ($A_c$) of freshly made chlorpyrifos as standardizing compound and also with a known amount ($A_{sc}$) of a stable standardizing compound (e.g., diethylchlorothiophosphate), such that the same signal, S, is generated by chlorpyrifos and the stable standardizing compound (e.g., In Example 1 below, the signal is the absorbance at 450 nm). The assay must be done under conditions where a change in chlorpyrifos concentration will result in a change in signal and a change in the stable standardizing compound concentration will result in a change in signal. If one then takes a sample with an unknown amount of analyte and obtains the same signal as obtained with an amount $A_{sc}$ of stable standardizing compound, then one would conclude that the analyte in the sample is chlorpyrifos in an amount equal to $A_c$.

If chlorpyrifos were stable under storage, it would not be necessary for purposes of analyzing for chlorpyrifos to also do the assay with a stable standardizing compound other than chlorpyrifos. As shown in Example 1, however, chlorpyrifos is not stable upon storage. Therefore it is better to use a stable standardizing compound (e.g., diethyl 4-methylbenzylphosphonate) as the standard when measuring a sample with unknown amounts of chlorpyrifos.

The foregoing procedures can be used with assays where the analyte is a phosphorothioate compound other than chlorpyrifos.

A related invention is a kit for an immunoassay in which the analyte is said kit comprising a standardizing compound that is either or or

An antibody used in steps (1) and (2) may be a polyclonal or monoclonal antibody. If the antibody is a polyclonal preparation, then in order to use antibodies of the same specificity in both steps (1) and (2), it is preferred that portions of the same aliquot of the preparation are used for steps (1) and (2). If the antibody is a monoclonal antibody generated by a hybridoma, then in order that antibodies of the same specificity be used in steps (1) and (2), it is preferred that antibodies from that hybridoma will be used for steps (1) and step (2).

Methods for monoclonal and polyclonal antibody production are well known in the art. For example, McAdam et al, *J. Agric. Food Chem.,* vol 40:1466–70 (1992), describes the use of rabbits for the production of polyclonal antibodies against organophosphate insecticides.

The invention and the standardizing compounds can be used in any assay format: competition assays (as in Example 1 below) where the analyte competes with labeled chlorpyrifos for the binding sites provided by the anti-chlorpyrifos antibody; non-competition assays, where the analyte does not compete for such binding sites; sandwich assays, where one anti-analyte antibody acts as a bridge to bind the analyte to a solid phase, and a second anti-analyte antibody with a detectable label is allowed to attach to the solid phase-bound analyte; or any other immunoassay format. Indeed the term "immunoassay" is intended here in a very general sense and is any assay in which an antibody specific for a phosphorothioate analyte of interest is used.

ASSAY GUIDELINES

Diluted samples should be kept on ice and assayed as soon as possible. All other reagents, including the standards and control, should be at room temperature prior to use. Sample dilutions should be made using Diluent/Zero Standard and mixed thoroughly prior to assaying.

"Color Reagent" is prepared just prior to use by combining 1 volume of Chromogen solution with one volume of Peroxide solution. The Color Reagent is prepared in a clean glass container and should remain clear.

The solution of antibody-coupled particles should not be in glass containers.

Reagents are added directly to the bottom of a tube while avoiding contact between the reagents in the tube and the pipet tip or droplets attached to the pipet tip. Cross-contamination and carry-over of reagents is avoided by using clean pipers for each sample addition. Foam formation during vortexing is undesirable.

A magnetic separator (e.g., the RAPID Magnetic Separator) consists of two parts: an upper rack which securely holds the test tubes and a lower part which contains magnets used to attract the antibody-coupled magnetic particles. The rack is described and illustrated in J.A. Itak et al, *Chemosphere,* vol 24, pp 11–21 (1992). During incubations the upper rack is removed from the lower part of the magnetic separator so that the magnetic particles remain suspended during the incubation. For separation steps, the rack and the lower part of the separator are combined to pull the magnetic particles to the walls of the tubes. To obtain optimum assay precision, it is important to perform the separation steps carefully and consistently. The rack is decanted by inverting it using a smooth turning action so that the liquid flows consistently along one side of the test tube. While still inverted, the rack is placed on an absorbent pad and allowed to drain. Lifting the rack and replacing gently into the pad several times will ensure complete removal of the liquid from the rim of the tube. The antibody-coupled magnetic particles should be mixed just prior to pipetting.

EXAMPLES

EXAMPLE 1

The assay was performed as follows:

Attachment of anti-chlorpyrifos antibodies to magnetic particles was done as follows: One ml of a 50 mg/ml suspension of BioMag 4100 amine-terminated particles (Advanced Magnetics, Cambridge, Mass.) were activated with 5% (v/v) glutaraldehyde in 2 ml of 0.01M MES buffer, pH 6 (MES is 2-(N-morpholino)ethanesulfonic Acid) for 3 hours. Unreacted glutaraldehyde was removed by washing four times with 5 ml of 0.01M MES buffer. Goat anti-mouse IgG serum was diluted to an antibody concentration of 5 mg/ml and 1 ml was reacted with the activated magnetic particles by shaking for 16 hours. A 1M glycine solution was then used to quench any unreacted sites for 30 minutes. The particles were then washed four times with 5 ml of 25 mM Tris, 150 mM NaCl, 0.1% BSA, 15 ppm Kathon (octhilinone, Rohm & Haas), 1 mM EDTA, pH 7.4. Particles were diluted so as to achieve an iron concentration of 8–10 mg/ml and stored in 25 mM Tris/150 mM NaCl, 0.1% bovine serum albumin (BSA), 15 ppm Kathon, 1 mM ethylenediaminetetraacetic acid (EDTA), pH 7.4. The magnetic particles (with bound antibody), were diluted 1:1000 in 150 mM Tris, 150 mM NaCl 0.1% Gel (fish gelatin, Sigma, St. Louis, Mo., Cat #G7765), 15 ppm active Kathon, 1 mM EDTA, pH 7.4. To the diluted particles, a 1:100,000 dilution of a solution of anti-chlorpyrifos monoclonal antibody serum (21.6 mg/ml of antibody) was added and incubated at room temperature (about 25° C.) for at least 16 hours.

Chlorpyrifos enzyme conjugate was chlorpyrifos conjugated to horse radish peroxidase (HRP) and was diluted to a concentration of approximately 18 ng/ml in 25 mM sodium acetate, 150 mM NaCl, 0.1 mM luminol (3-aminophthalhydrazide), 0.1% gel, 15 ppm Kathon, pH 5.0.

Each standardizing compound was dissolved or diluted in methanol to obtain a concentration of 10 mg/ml and then diluted to the specified concentration in "Diluent/Zero Standard" (25 mM sodium acetate, 150 mM NaCl, 0.1% gel, 0.1 mM EDTA, 15 ppm Kathon, pH 4.0).

Peroxide solution was a 0.02% solution of hydrogen peroxide in citric buffer, pH 4.5. (Obtained from Kirkegaard & Perry Laboratories, Gaithersburg, Md.)

Chromogen solution was 0.4 g/ml of 3,3'5,5'tetramethylbenzidine ("TMB") in 26% dimethylformamide. (Obtained from Kirkegaard & Perry Laboratories, Gaithersberg, Md.).

"Stopping Solution" was 2M sulfuric acid.

Washing Buffer was 25 mM Tris, 150 mM NaCl, 0.1% gel, 0.1% Tween, 15 ppm Kathon, pH 7.4.

Polystyrene test tubes were used.

Anti-chlorpyrifos antibody was prepared by using a chlorpyrifos-thyroglobulin (porcine) immunogen whose structure is:

wherein the amine moiety on the thyroglobulin is contributed by a primary amine of that protein. Balb/c mice were immunized by injecting them subcutaneously with 200 ug of the chlorpyrifos-thyroglobulin immunogen in Freund's complete adjuvant. Three 100 ug subcutaneous injections with Freund's incomplete adjuvant followed, 3, 5 and 6 weeks after initial immunization. Three weeks after the last injection, a 100 ug i.p. injection was given in phosphate buffer saline. Mice were sacrificed, spleens were removed and their cells fused with PEG (polyethylene glycol) to P3X myeloma cells. Following screening and recloning, appropriate hybridomas were grown as ascites tumors in mice.

Assay Procedure:

1) Added 200 uL (microliters) of chlorpyrifos, standardizing compound, or control ("diluent zero standard") to a test tube;
2) Added 250 uL of chlorpyrifos-HRP conjugate 1:70,000 dilution to the test tube of step (1);
3) Added 500 uL of magnetic particles coupled to anti-chlorpyrifos antibodies to each tube and vortexed the test tube of step (2).
4) Incubated the test tube for 15 minutes at room temperature (about 25° C.).
5) Magnetically separated the particles and substances bound thereto from the other contents of the tube; the particle-free solution was decanted and the particles were washed twice with 1 ml of Washing Solution.
6) Added 500 uL of Color Reagent and vortexed the test tube.
7) Incubated the test tube for 20 minutes at room temperature.
8) Read the absorbance at 450 nm using an RPA-I™ photometer.

For graphical display of the results, the quantity B/Bo for a given concentration of chlorpyrifos or standardizing compound was calculated: $B/Bo_o$ is the absorbance at 450 nm observed for chlorpyrifos or a standardizing compound at that concentration divided by the absorbance at 450 nm observed with zero standard (just "Diluent Standard Buffer" buffer).

The following four samples were tested:

1) chlorpyrifos (a "test compound")
2) diethyl 4-methylbenzylphosphonate (a "standardizing compound")
3) N-methyl-3,5,6-trichloro-2-pyridinone (a "standardizing compound")
4) diethyl chloro thiophosphate (a "standardizing compound")

Figure 1:
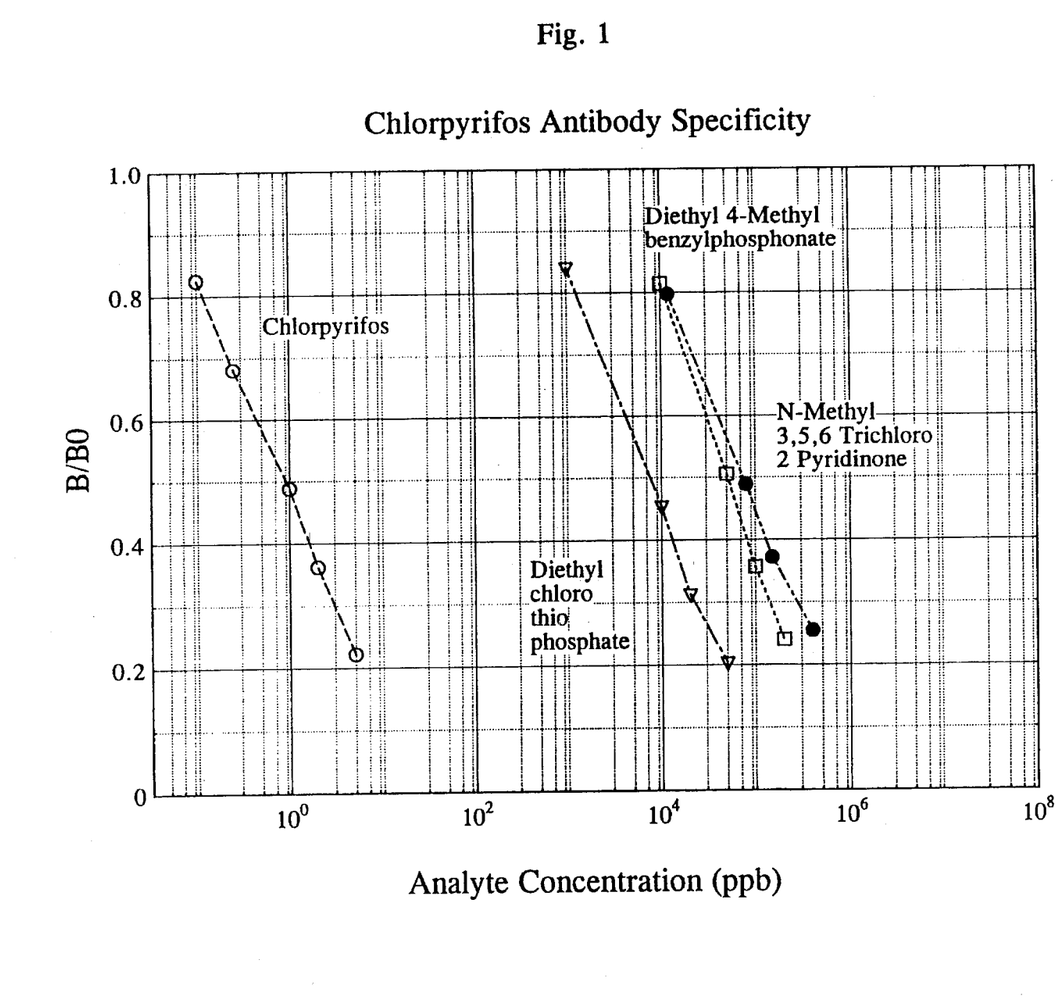
FIG. 1. Immunoassay standardization curves.
Figure 2:
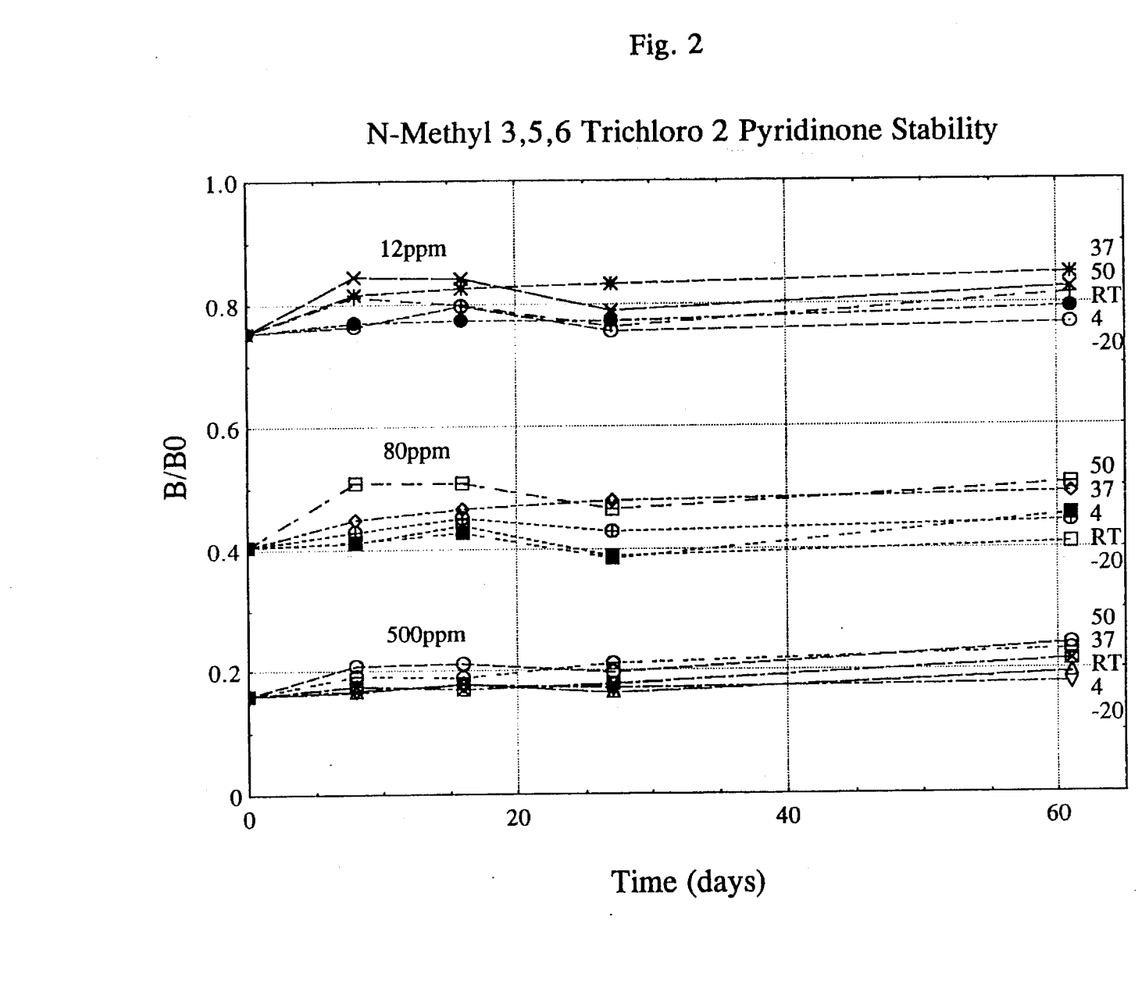
FIG. 2. Reactivity of N-methyl-3,5,6-trichloro-2-pyridinone in the immunoassay as a function of time and temperature of storage of that compound.
Figure 3:
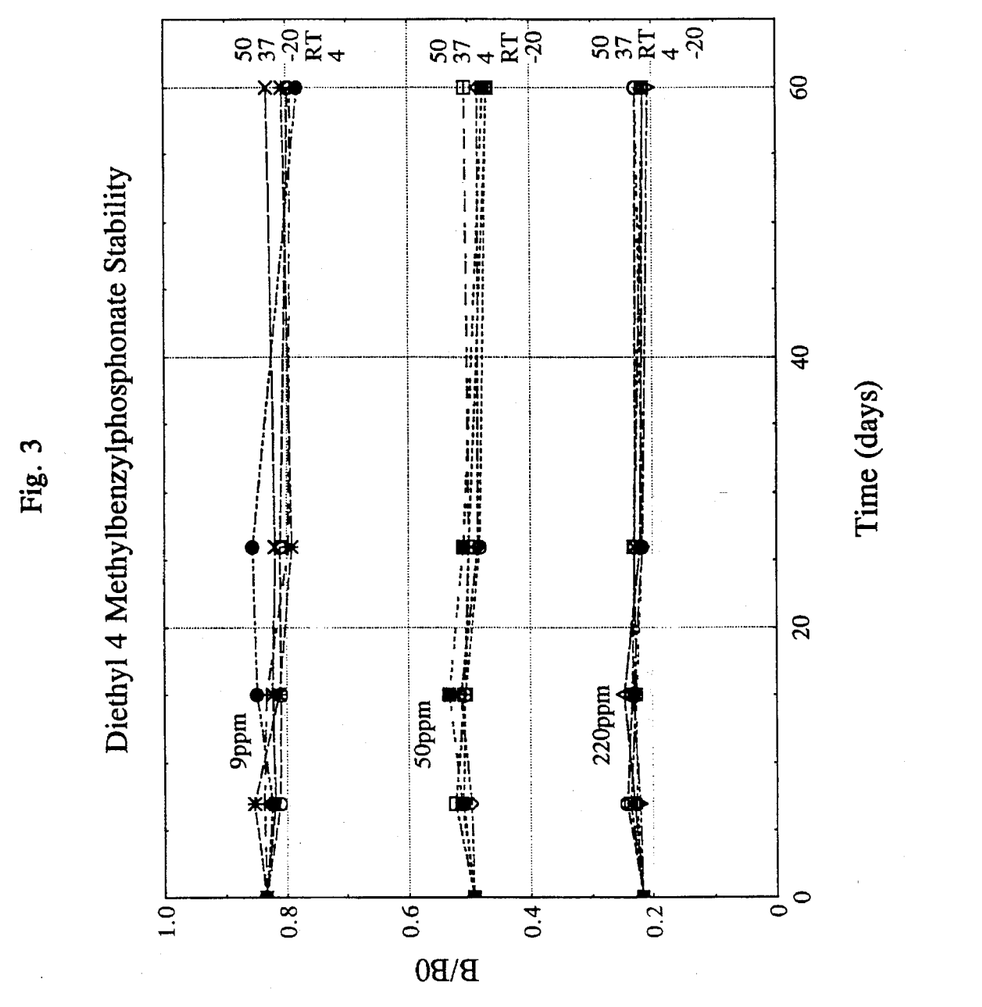
FIG. 3. Reactivity of diethyl 4-methylbenzylphosphonate in the immunoassay as a function of time and temperature of storage of that compound.
Figure 4:
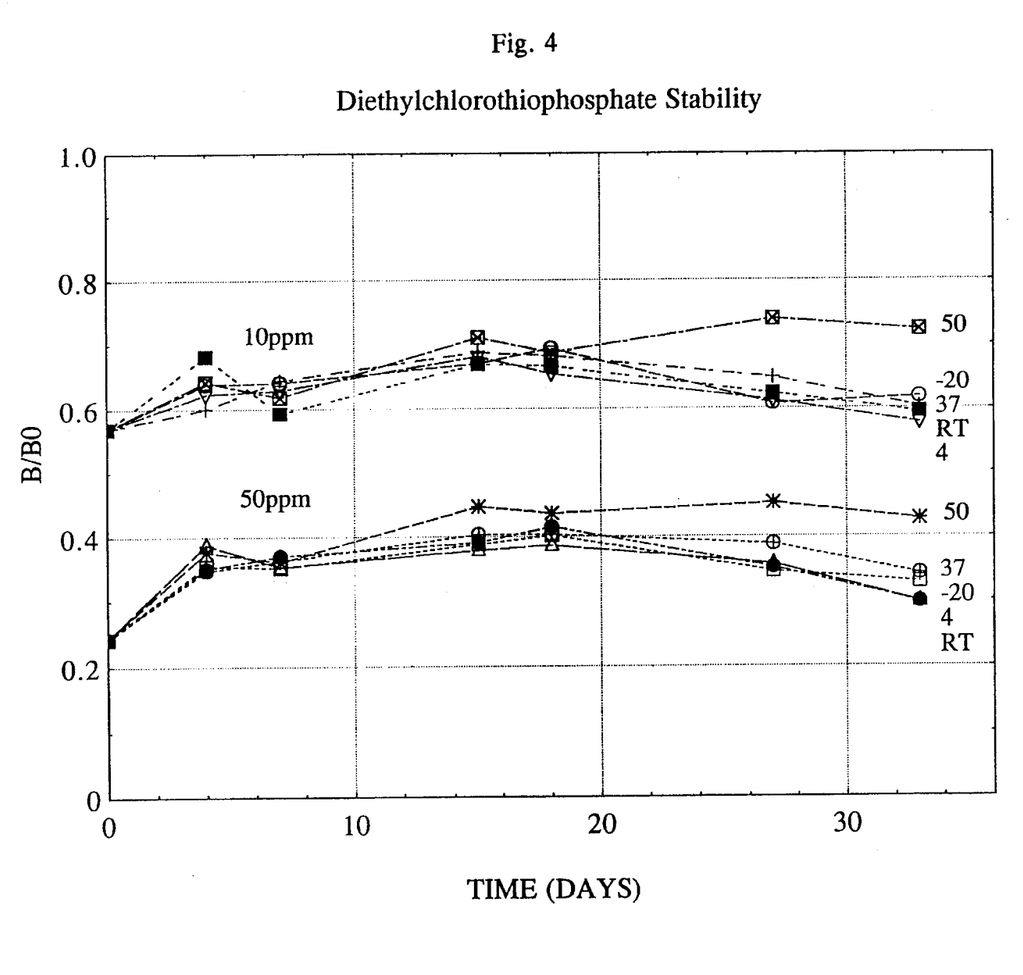
FIG. 4. Reactivity of the compound, diethylchlorothiophosphate, in the immunoassay as a function of time and temperature of storage of that compound.
Figure 5:
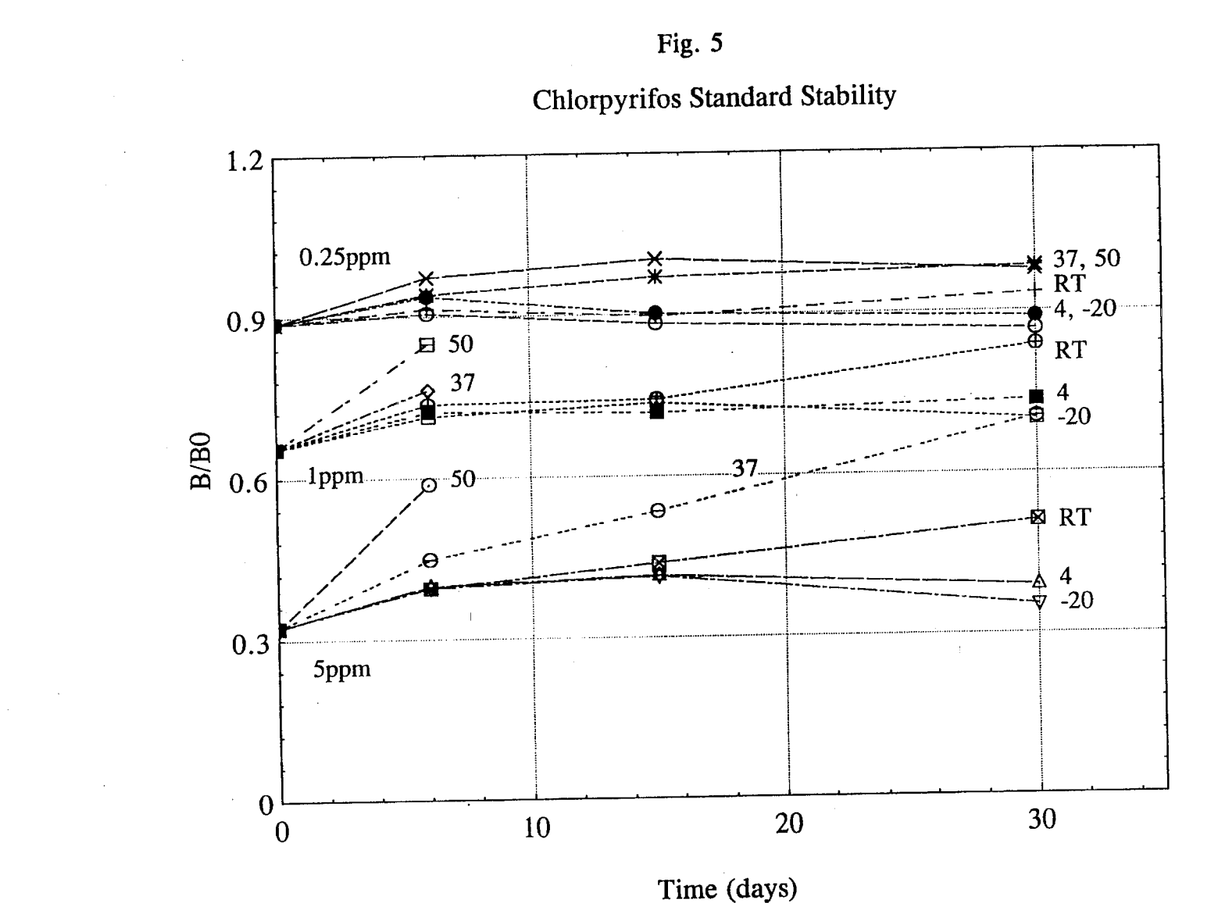
FIG. 5. Reactivity of the compound, chlorpyrifos, in the immunoassay as a function of time and temperature of storage of that compound.

The results are shown in FIG. 1 where B/Bo is shown as a function of the ppb (parts per billion) of the sample in the assay.

FIGS. 2, 3, 4, and 5, show the value of B/Bo as a function of how long the chlorpyrifos was stored prior to testing in the assay. The temperature of storage, either 50, 37, RT (room temperature), 4, or minus 20° C. The temperature of storage is shown at the right end of each line describing the stability. The concentrations of the various compounds were:

12 ppM, 80 ppM, and 500 ppM for N-methyl-3,5,6-trichloro-2-pyridinone 9 ppM, 50 ppM, and 220 ppM for diethyl 4omethylbenzylphosphonate 10 ppM, and 50 ppM (parts per million) for diethylchlorothiophosphate 0.25 ppB (parts per billion), 1 ppB, and 5 ppB for chlorpyrifos The results show that diethyl 4-methylbenzylphosphonate, N-methyl-3,5,6-trichloro-2-pyridinone, and diethylchlorothiophosphate, are more stable than chlorpyrifos.

The results also show the following regarding the relative reactivity of chlorpyrifos and the three standardizing compounds: that 1 ppB of chlorpyrifos was equivalent to 50 ppm of diethyl 4-methylbenzylphosphonate, to 8 ppm of diethylchlorothiophosphate, and to 75 ppm of N-methyl-3,5,6-trichloro-2-pyridinone.

EXAMPLE 2

Example 1 is performed except that instead of chlorpyrifos, samples with an unknown amount of chlorpyrifos is used. The results (B/Bo) are used to calculate the amount of chlorpyrifos in the sample for those samples that have chlorpyrifos in the chlorpyrifos concentration range tested in FIG. 1.

What is claimed is:

1. An immunoassay process comprising the steps of:
   1) reacting a sample with an antibody, said sample comprising an amount of analyte, said antibody reactive against said analyte,
   2) reacting a known amount of a standardizing compound with an antibody of the same specificity as that used in step (1),
   3) quantitating the amount of antibody that reacted with the sample in step (1);
   4) quantitating the amount of antibody that reacted with the standardizing compound in step (2);
   5) utilizing the amounts quantitated in steps (3) and (4) and the known amount in step (2) to calculate the amount of analyte present in the sample used in step (1), wherein the analyte is wherein the standardizing compound is either or or wherein $X_1$ is C or N, $X_2$ is C if $X_1$ is C, $X_2$ is C or N if $X_1$ is N,

$R_1$ is $C_1$–$C_4$ alkyl, $R_2$ is H, $C_1$–$C_4$ alkyl, $NO_2$, a dialkylamino that is di($C_1$–$C_4$ alkyl)amino, Cl, Br, I, ($C_1$–$C_4$ alkyl)—S—, $C_1$–$C_4$ alkyl-(O=S)—, —$SO_2NH_2$, or —S—$R_5$, provided that $R_2$ is —S—$R_5$ only if $X_1$ and $X_2$ are both C and $R_2$ is in the para position (4-position on the benzene ring)

$R_3$ is H, Cl, Br, or I, $R_4$ is H, Cl, Br, or I, $R_5$ is wherein $R_6$ is $C_1$–$C_4$ alkyl, $R_7$ is Cl, Br, I, OH, $(CH_2)_mCH_3$, benzyl or benzyl substituted with I, Cl, Br, $CH_3$, $OCH_3$, $O(CH2)_mCH_3$, and m is an integer in the range 1 through 10 (i.e., 1, 2, 3, 4, 5, 6, 7, 8, 9, or 10)

$R_8$ is O, NH, or S, $R_9$ is H or $C_1$–$C_4$ alkyl, $R_{10}$ is Cl, Br, I, $CH_3$, $(CH_2)_qCH_3$, $OCH_3$, or $O(CH_2)_qCH_3$, and q is an integer in the range 1 through 10, $R_{11}$ is $(CH_2)_y$, and y is an integer in the range 1 through 10

$R_{12}$ is O, NH, or S, $R_{13}$ is $CH_3$, $(CH_2)_zCH_3$, $OCH_3$, or $O(CH_2)_zCH_3$ and wherein z is an integer in the range 1 through 10, $R_{14}$ is Cl, I or Br, $R_{15}$ is H, Cl, Br, or I, $R_{16}$ is H, Cl, Br, or I, provided that $R_2$, $R_3$, and $R_4$, are not joined to $X_1$ if it is N or to $X_2$ if it is N.

2. The immunoassay process of claim 1 wherein the analyte is chlorpyrifos, chlorpyrifos-methyl, diazinon, fenitrothion, parathion-methyl, parathion, fensulfothion, fenthion, pyrimiphos-ethyl, pyrimiphos-methyl, dicapthon, cythioate, or temephos.

3. The immunoassay process of claim 1 wherein the standardizing compound is selected from the group consisting of N-methyl-3,5,6-trichloro-2-pyridinone, diethyl 4-methylbenzylphosphonate, and diethylchlorothiophosphate.

4. The immunoassay process of claim 3 wherein the standardizing compound is N-methyl-3,5,6-trichloro-2-pyridinone.

5. The immunoassay process of claim 3 wherein the standardizing compound is diethyl 4-methylbenzylphosphonate.

6. The immunoassay process of claim 3 wherein the standardizing compound is diethylchlorothiophosphate.

7. The immunoassay process of claim 2 wherein the standardizing compound is selected from the group consisting of N-methyl-3,5,6-trichloro-2-pyridinone, diethyl 4-methylbenzylphosphonate and diethylchlorothiophosphate.

8. The immunoassay process of claim 7 wherein the standardizing compound is N-methyl-3,5,6-trichloro-2-pyridinone.

9. The immunoassay process of claim 7 wherein the standardizing compound is diethyl 4-methylbenzylphosphonate.

10. The immunoassay process of claim 7 wherein the standardizing compound is diethylchlorothiophosphate.

11. A process of claim 1 wherein $R_8$ is O or S and wherein $R_{12}$ is O or S.

12. A process of claim 1 wherein $R_8$ is S and wherein $R_{12}$ is S.

13. A process of claim 11 wherein the standardizing compound is

14. A process of claim 11 wherein the standardizing compound is

15. A process of claim 11 wherein the standardizing compound is

16. A process of claim 11 wherein $R_{13}$ is $CH_3$, $(CH_2)_zCH_3$ or $OCH_3$ and wherein $R_{10}$ is Cl, Br, I, $CH_3$, $(CH_2)_qCH_3$, $OCH_3$, or $O(CH_2)CH_3$, and q is an integer in the range 1 through 10.

17. A process of claim 12 wherein $R_{13}$ is $CH_3$, $(CH_2)_zCH_3$ or $OCH_3$ and wherein $R_{10}$ is Cl, Br, I, $CH_3$, $(CH_2)_qCH_3$, $OCH_3$, or $O(CH_2)CH_3$, and q is an integer in the range 1 through 10.

18. A process of claim 11 wherein $R_2$ is dialkylamino, $X_1$ and $X_2$ are both N atoms, and $R_2$ is adjacent to the carbon on the aromatic ring immediately adjacent to both of said N atoms.

19. A process of claim 11 wherein $R_2$ is $NO_2$, $C_1$–$C_4$ alkyl-S—, $C_{1-C4}$ alkyl-(O=S)—or —$SO_2NH_2$, wherein $X_1$ and $X_2$ are both C, and $R_2$ is at the 4position on the aromatic ring.

20. A process of claim 19 wherein $R_3$ and $R_4$ are both H.

21. A process of claim 11 wherein $R_3$ is Cl, Br, or I, and wherein $R_2$ and $R_4$ are both either H, Cl, Br, or I.

22. A process of claim 21 wherein $R_2$, $R_3$, and $R_4$ are the same.

23. A process of claim 14 wherein $R_{15}$ is Cl, Br, or I, and both $R_{10}$ and $R_{16}$ are either H, Cl, Br, or I.

24. A process of claim 23 wherein $R_{10}$, $R_{15}$, and $R_{16}$ are the same.

25. A process of calibrating a standardizing compound relative to a test compound of interest in an immunoassay of interest, said process comprising the steps of:
  1) reacting a known amount of test compound with an antibody,
  2) reacting under the immunoassay conditions of step (1) a known amount of a standardizing compound with an antibody of the same specificity as that used in step (1) (i.e., same immunoassay conditions as step (1) except that the test compound has been replaced with the standardizing compound),
  3) quantitating the amount of antibody that reacted with the test compound in step (1);
  4) quantitating the amount of antibody that reacted with the standardizing compound in step (2);
  5) utilizing the amounts quantitated in steps (3) and (4) and the known amounts of steps (1) and (2) to calculate the relative reactivity of the standardizing compound and the test compound under the immunoassay conditions of step (1), wherein the test compound is wherein the standardizing compound is either or or wherein $X_1$ is C or N, $X_2$ is C if $X_1$ is C, $X_2$ is C or N if $X_1$ is N,

$R_1$ is $C_1$–$C_4$ alkyl, $R_2$ is H, $C_1$–$C_4$ alkyl, $NO_2$, a dialkylamino that is di($C_1$–$C_4$ alkyl)amino, Cl, Br, I, ($C_1$–$C_4$ alkyl)—S—, $C_1$–$C_4$ alkyl-(O=S)—, —$SO_2NH_2$, or —S—$R_5$, provided that $R_2$ is —S—$R_5$ only if $X_1$ and $X_2$ are both C and $R_2$ is in the para position (4-position on the benzene ring)

$R_3$ is H, Cl, Br, or I, $R_4$ is H, Cl, Br, or I, $R_5$ is wherein $R_6$ is $C_1$–$C_4$ alkyl, $R_7$ is Cl, Br, I, OH, $(CH_2)_mCH_3$, benzyl or benzyl substituted with I, Cl, Br, $CH_3$, $OCH_3$, $O(CH2)_mCH_3$, and m is an integer in the range 1 through 10 (i.e., 1, 2, 3, 4, 5, 6, 7, 8, 9, or 10)

$R_8$ is O, NH, or S, $R_9$ is H or $C_1$–$C_4$ alkyl, $R_{10}$ is Cl, Br, I, $CH_3$, $(CH_2)_qCH_3$, $OCH_3$, or $O(CH_2)_qCH_3$, and q is an integer in the range 1 through 10, $R_{11}$ is $(CH_2)_y$, and y is an integer in the range 1 through 10

$R_{12}$ is O, NH, or S, $R_{13}$ is $CH_3$, $(CH_2)_zCH_3$, $OCH_3$, or $O(CH_2)_zCH_3$ and wherein z is an integer in the range 1 through 10, $R_{14}$ is Cl, I or Br, $R_{15}$ is H, Cl, Br, or I, $R_{16}$ is H, Cl, Br, or I, provided that $R_2$, $R_3$, and $R_4$, are not joined to $X_1$ if it is N or to $X_2$ if it is N.

26. A process of claim 25 wherein $R_8$ is O or S and wherein $R_{12}$ is O or S.

27. A process of claim 26 wherein $R_{13}$ is $CH_3$, $(CH_2)_zCH_3$ or $OCH_3$ and wherein $R_{10}$ is Cl, Br, I, $CH_3$, $(CH_2)_qCH_3$, $OCH_3$, or $O(CH_2)CH_3$, and q is an integer in the range 1 through 10.

28. The immunoassay process of claim 25 wherein the analyte is chlorpyrifos, chlorpyrifos-methyl, diazinon, fenitrothion, parathion-methyl, parathion, fensulfothion, fenthion, pyrimiphos-ethyl, pyrimiphos-methyl, dicapthon, cythioate, or temephos.

29. The process of claim 25 wherein the standardizing compound is selected from the group consisting of N-methyl-3,5,6-trichloro-2-pyridinone, diethyl 4-methylbenzylphosphonate, and diethylchlorothiophosphate.

30. The process of claim 29 the standardizing compound is N-methyl-3,5,6-trichloro-2-pyridinone.

31. The process of claim 29 wherein the standardizing compound is diethyl 4-methylbenzylphosphonate.

32. The process of claim 29 wherein the standardizing compound is diethylchlorothiophosphate.

33. The immunoassay process of claim 28 wherein the standardizing compound is selected from the group consisting of N-methyl-3,5,6-trichloro-2-pyridinone, diethyl 4-methylbenzylphosphonate, and diethylchlorothiophosphate.

34. The process of claim 33 the standardizing compound is N-methyl-3,5,6-trichloro-2-pyridinone.

35. The process of claim 33 wherein the standardizing compound is diethyl 4-methylbenzylphosphonate.

36. The process of claim 33 wherein the standardizing compound is diethylchlorothiophosphate.

37. A kit for an immunoassay in which the analyte is said kit comprising an antibody reactive against said analyte, said kit further comprising a standardizing compound that is either or or wherein $X_1$, is C or N, $X_2$, is C if $X_1$ is C, $X_2$ is C or N if $X_1$ is N,

$R_1$, $C_1$–$C_4$ alkyl, $R_2$ is H, $C_1$–$C_4$ alkyl, $NO_2$, a dialkylamino that is di($C_1$–$C_4$ alkyl)amino, Cl, Br, I ($C_1$–$C_4$ alkyl)—S—, $C_1$–$C_4$ alkyl-(O=S)—, —$SO_2NH_2$, or —S—$R_5$, provided that $R_2$ is —S— only if $X_1$, and $X_2$ are both C and $R_2$ is in the para position (4-position on the benzene ring)

$R_3$ is H, Cl, Br, or I, $R_4$, is H, Cl, Br, or I, $R_5$ is wherein $R_6$ is $C_1$–$C_4$ alkyl, $R_7$ is Cl, Br, I, OH, $(CH_2)_m CH_3$, benzyl or benzyl substituted with I, Cl, Br, $CH_3$, $OCH_3$, $O(CH_2)_m CH_3$, and m is an integer in the range 1 through 10 (i.e., 1, 2, 3, 4, 5, 6, 7, 8, 9, or 10)

$R_8$ is O, NH, or S, $R_9$ is H or $C_1$–$C_4$ alkyl, $R_{10}$ is Cl, Br, I, $CH_3$, $(CH_2)_q CH_3$, $OCH_3$, or $O(CH_2)_q CH_3$, and q is an integer in the range 1 through 10, $R_{11}$ is $(CH_2)_y$, and y is an integer in the range 1 through 10

$R_{12}$ is O, NH, or S, $R_{13}$ is $CH_3$, $(CH_2)_z CH_3$, $OCH_3$, or $O(CH_2)_z CH_3$ and wherein z is an integer in the range 1 through 10, $R_{14}$ is Cl, I or Br, $R_{15}$ is H, Cl, Br, or I, $R_{16}$ is H, Cl, Br, or I, provided that $R_2$, $R_3$, and $R_4$, are not joined to $X_1$ if it is N or to $X_2$ if it is N.

38. A kit of claim 37 wherein $R_8$ is O or S and wherein $R_{12}$ is O or S.

39. A kit of claim 38 wherein $R_{13}$ is $CH_3$, $(CH_2)_z CH_3$ or $OCH_3$ and wherein $R_{10}$ is Cl, Br, I, $CH_3$, $(CH_2)_q CH_3$, or $O(CH_2)CH_3$, and q is an integer in the range 1 through 10.

* * * * *